United States Patent
Gharib

(10) Patent No.: US 7,255,680 B1
(45) Date of Patent: Aug. 14, 2007

(54) POSITIVE PRESSURE INFUSION SYSTEM HAVING DOWNSTREAM RESISTANCE MEASUREMENT CAPABILITY

(75) Inventor: James E. Gharib, San Diego, CA (US)

(73) Assignee: Cardinal Health 303, Inc., San Diego, CA (US)

( * ) Notice: Subject to any disclaimer, the term of this patent is extended or adjusted under 35 U.S.C. 154(b) by 0 days.

(21) Appl. No.: 09/428,006

(22) Filed: Oct. 27, 1999

(51) Int. Cl.
*A61M 31/00* (2006.01)
(52) U.S. Cl. .......................................... 604/67
(58) Field of Classification Search ................. 604/67, 604/113, 4.01–6.01, 65, 131, 132, 140, 141; 607/96, 104, 105, 106, 113, 114
See application file for complete search history.

(56) References Cited

U.S. PATENT DOCUMENTS

| | | | |
|---|---|---|---|
| 3,648,694 A | 3/1972 | Mogos et al. ............. 128/214 F |
| 3,895,741 A | 7/1975 | Nugent ........................ 222/103 |
| 4,447,224 A * | 5/1984 | DeCant et al. ................. 604/67 |
| 4,530,696 A | 7/1985 | Bisera et al. ................ 604/253 |
| 4,613,327 A | 9/1986 | Tegrarian et al. ............ 604/141 |
| RE32,294 E | 11/1986 | Knute .......................... 604/253 |
| 4,626,241 A | 12/1986 | Campbell et al. .............. 604/49 |
| 4,661,246 A * | 4/1987 | Ash ................................ 210/87 |
| 4,718,022 A * | 1/1988 | Cochran ...................... 364/510 |
| 4,816,019 A | 3/1989 | Kamen ........................... 604/65 |
| 4,898,576 A | 2/1990 | Philip ............................ 604/50 |
| 4,919,596 A | 4/1990 | Slate et al. .................... 417/18 |
| 5,096,385 A | 3/1992 | Georgi et al. ................. 417/18 |
| 5,163,909 A | 11/1992 | Stewart ........................ 604/140 |
| 5,277,820 A * | 1/1994 | Ash .............................. 210/646 |
| 5,308,335 A | 5/1994 | Ross et al. ................... 604/141 |
| 5,348,539 A | 9/1994 | Herskowitz .................. 604/141 |
| 5,399,166 A | 3/1995 | Laing .......................... 604/146 |
| 5,411,482 A | 5/1995 | Campbell ..................... 604/153 |
| 5,433,704 A | 7/1995 | Ross et al. ..................... 604/67 |
| 5,584,811 A * | 12/1996 | Ross et al. ................... 604/141 |
| 5,609,576 A | 3/1997 | Voss et al. ..................... 604/67 |
| RE35,501 E | 5/1997 | Ross et al. ................... 604/141 |
| 6,156,007 A * | 12/2000 | Ash .............................. 604/113 |

FOREIGN PATENT DOCUMENTS

FR        2 592 306 A1    7/1987

\* cited by examiner

*Primary Examiner*—Kevin C. Sirmons
*Assistant Examiner*—Bhisma Mehta
(74) *Attorney, Agent, or Firm*—Fulwider Patton LLP

(57) ABSTRACT

A fluid delivery system includes a first fluid container having infusion fluid for a patient. The first fluid container has an outlet and a conduit attached to the outlet. A second fluid container applies pressure to the first fluid container to force fluid out of the first container and into the conduit at a desired flow rate. A pressure sensor is coupled to the second fluid container and a flow sensor is coupled to the conduit. The processor monitors the flow rate and controls the duty cycle of a downstream flow control actuator to maintain the desired flow rate. The processor determines the downstream resistance of the system by varying the flow rate about the selected flow rate, receiving pressure signals from the pressure sensor and flow signals from the flow sensor, and calculating the change in pressure over the change in flow rate to produce the fluid resistance measurement.

40 Claims, 5 Drawing Sheets

POSITIVE PRESSURE INFUSION SYSTEM HAVING DOWNSTREAM RESISTANCE MEASUREMENT CAPABILITY

BACKGROUND OF THE INVENTION

The invention relates generally to fluid delivery systems, and more particularly, to an intravenous (IV) infusion system having a positive-pressure based mechanism for inducing fluid flow and a monitoring system for measuring the downstream resistance of the IV infusion system based on changes in pressure and flow rate.

IV infusion systems for infusing fluid to a patient typically include a supply of fluid for administration, an infusion needle or cannula, an administration set connecting the fluid supply to the cannula, and a flow control device. The administration set typically includes a flexible IV tube and a drip chamber. The cannula is mounted at the distal end of the flexible IV tubing for insertion into a patient's blood vessel or other body location to deliver the fluid to the patient.

The flow control device may be either gravity-pressure based or positive-pressure based. Gravity-pressure based flow control devices rely on the force of gravity for fluid flow. These devices may include an "IV controller" which interfaces with the IV tube. An IV controller is a device that automatically controls the flow rate of fluid through the IV tube by use of a pinching device that pinches the tube more or less to control the flow of fluid therethrough. The IV controller is usually responsive to a control signal which is typically generated by a flow sensor attached to the drip chamber. The flow sensor senses fluid drops falling in the drip chamber. The number of drops per unit time is counted and a flow rate calculated. If the calculated flow rate is greater than a desired flow rate, the controller adjusts the pinching device to lower the flow rate by pinching the tube further. Advantages of gravity administration sets include their relative simplicity and low cost. Relatively inexpensive tubing may be used such as polyvinyl chloride ("PVC") tubing or similar type tubing. The pinching device comprises a relatively simple mechanical device under electrical control. IV controllers, however, are limited to gravity pressure, dependent upon the "head height" or "head pressure" of the administration fluid, which can be under 1 psi.

In certain situations the amount of pressure provided by a gravity-pressure based flow control device may be insufficient. In other situations, greater accuracy and precision of flow rates are required. In these situations a positive-pressure based flow control device is necessary. Positive-pressure based flow control devices exert a mechanical force on the fluid to establish fluid flow. One commonly used positive-pressure based flow control device is a linear peristaltic pump. A linear peristaltic pump is a complex device comprising several cams and cam-actuated fingers that sequentially occlude portions of the flexible tubing along a specially designed pumping segment to create a moving zone of occlusion. The peristaltic action forces the fluid through the tubing of the administration set to the cannula and into the patient. Because of its complexity and number of components, a linear peristaltic type pump is relatively expensive and may be undesirable in situations where cost containment is a factor. The pumping segment is also typically part of a disposable administration set and thus is relatively expensive.

Another type of positive-pressure based flow control device is a piston-and-valve-type device that uses a specially designed plastic cassette or cylinder device that interfaces with the piston and valve to control fluid flow. The cassette or cylinder is small in size and has precise dimensional requirements so as to provide accurate fluid flow control. Due to such requirements these devices are expensive to manufacture. The cassette or cylinder is also typically part of a disposable administration set and thus have an increased cost.

Another type of positive-pressure based flow control device includes a collapsible fluid treatment bag and an inflatable bladder. A fluid pump or other pressure source provides fluid, typically air, to the bladder. As the bladder inflates, pressure is applied to the collapsible fluid treatment bag. This pressure forces fluid through the tubing of the administration set to the cannula and into the patient.

During infusion events may occur that interfere with the proper administration of fluid to the patient, such as an occlusion of the administration line. It is desirable to detect these conditions as soon as possible so that they can be remedied. A commonly used technique for detecting such conditions and for evaluating the operating status of the IV infusion system is to monitor the pressure in the downstream portion of the fluid delivery tube. The "downstream" portion of the tube is typically thought of as the portion between the flow control device, such as the pinching device in a controller or the peristaltic fingers in a linear peristaltic pump, and the patient's blood vessel. An increase in the downstream pressure may be caused by an occlusion.

One measurement of downstream infusion system parameters that has proved useful is a measurement of resistance. Downstream resistance may be affected by a downstream occlusion, an infiltration of the cannula into the patient's tissue surrounding the blood vessel, a cannula that has become removed from the blood vessel, or others. By monitoring downstream resistance, an operator may be able to determine if any of the above events has occurred. Appropriate steps may be taken to remedy the situation sooner than with other monitoring approaches. It should be noted that when the cannula is in place in a patient's blood vessel, that blood vessel also contributes an effect to the flow and pressure in the tubing and is therefore considered part of the downstream resistance.

Sophisticated flow control devices monitor the downstream resistance of the infusion system by altering the flow rate through the tube and measuring the corresponding change in downstream pressure. The change in pressure over the change in the flow rate has been found to accurately indicate the resistive part of the downstream fluid impedance. In these systems, a pressure sensor is coupled to the infusion tube. The pressure sensor monitors the pressure existing in the downstream portion of the tube and produces pressure signals representing the detected pressure.

A disadvantage of these existing systems for detecting downstream resistance is that the pressure sensor must be coupled to the IV tube. Because of this, the pressure sensors must be capable of accurately detecting fluid pressure through an IV tube. Such sensors tend to be complex and expensive.

Hence, those skilled in the art have recognized a need for a simpler and less expensive positive-pressure based IV infusion system. Those skilled in the art have also recognized the need for an administration set using standard tubing and a standard flow monitoring system, such as a drip chamber, with a standard collapsible administration fluid container which may be accurately used with a positive pressure based IV infusion system. A need has also been recognized for a closed-loop positive-pressure based IV infusion system wherein flow rate and pressure can be monitored using standard administration set tubing and drip chamber devices for lowered cost. A further need has been recognized for a single integrated package design containing fluid source, flow sensing, flow control, pressure source, pressure sensing, and pressure control. The present invention fulfills these needs and others.

SUMMARY OF THE INVENTION

Briefly, and in general terms, the invention is directed to an apparatus and a method for controlling fluid flow through an IV infusion system and, in another aspect, for monitoring the downstream resistance of the IV infusion system.

In a first aspect, the invention is an apparatus for pumping infusion fluid from a first fluid container having an output communicating with a conduit. The apparatus includes a second fluid container for applying pressure to the first fluid container to expel fluid from the first fluid container, and a pressure sensor coupled to the second fluid container adapted to sense pressure in the second fluid container and provide pressure signals in response to the pressure sensed. The apparatus also includes a flow sensor coupled to the conduit and adapted to sense fluid flow in the conduit and provide flow signals in response to the fluid flow sensed, and a processor responsive to the pressure signals and flow signals for determining the downstream resistance of the conduit.

By providing a second fluid container, e.g., a fluid bladder, which applies pressure to a first fluid container to expel fluid from the first fluid container, a pressure sensor coupled to the second fluid container, and a flow sensor coupled to the conduit the present invention provides a pressure-based flow control device that is free of complicated and costly peristaltic or cassette pumping means. The flow control device also has the capability of determining the downstream resistance in the conduit communicating with the output of the first container through the use of a standard, readily available pressure sensor at the input of the second fluid container, as opposed to a complicated and costly pressure sensor attached to the downstream region of the conduit as is common in current flow control devices. Furthermore, since there are no cassette pumping means, a very simple and inexpensive straight line gravity IV set may be used.

In a more detailed aspect, the apparatus further includes a pump coupled to the second fluid container for controlling the pressure within the second fluid container. In another aspect, the apparatus further includes a flow control actuator coupled to the conduit downstream from the flow sensor. In still another facet, the processor determines the downstream resistance by setting a plurality of target flow rates, measuring the pressure applied to the fluid in the first container to cause each of the plurality of target flow rates to exist at the output of the first fluid container, receiving the flow data resulting from each target flow rate and determining the impedance. In yet another facet, the processor determines the downstream resistance by controlling the pressure applied to the first container to cause a plurality of different flow rates to exist at the output of the first fluid container, receiving the flow data resulting from each flow rate and determining the impedance by processing changes in applied pressure and changes in flow together.

In a second aspect, the invention is a fluid delivery system having a first fluid container with an outlet and a fluid conduit attached to the outlet. The system includes an input device for selecting a flow rate, a second fluid container for applying pressure to the first fluid container to expel the fluid from the first fluid container into the conduit, a pressure sensor coupled to the second fluid container adapted to sense pressure in the second fluid container and provide pressure signals in response to the pressure sensed, and a flow sensor coupled to the conduit and adapted to sense fluid flow in the conduit and provide flow signals in response to the fluid flow sensed. The fluid delivery system also includes a processor that varies the flow rate about the selected flow rate by varying the pressure applied to the first fluid container, receives the pressure signals and the flow signals, and calculates the downstream resistance of the system.

In a third facet, the invention is a fluid delivery system having a first fluid container with an outlet and a fluid conduit attached to the outlet. The system includes an input device for selecting a flow rate, a second fluid container for applying pressure to the first fluid container, and a pressure sensor coupled to the second fluid container and adapted to sense pressure and provide pressure signals in response to the pressure sensed. The system also includes a flow sensor coupled to the conduit and adapted to sense fluid flow in the conduit and provide flow signals in response to the fluid flow sensed, and a processor for maintaining the flow rate at a value substantially equal to the selected flow rate.

In a more detailed facet the flow rate is maintained by varying the pressure applied to the first fluid container. In another facet, the system includes a pump coupled to the second fluid container and the flow rate is maintained by varying the output of the pump. In yet another aspect, the flow rate is maintained by compressing the conduit. In still another facet, the system includes a flow control actuator coupled to the conduit and the flow rate is maintained by varying the flow of fluid through the conduit using the flow control actuator.

In a fourth aspect, the invention is an apparatus for delivering infusion fluid including a fluid container for holding infusion fluid that has an outlet and a tube attached to the outlet that is in fluid communication with the fluid container. The apparatus also includes a pressure bladder proximal the fluid container, for applying pressure to the fluid container to expel fluid from the fluid container into the tube, a pressure device for varying the pressure within the pressure bladder, a pressure sensor for monitoring the pressure within the pressure bladder and providing pressure data, a flow sensor for monitoring the flow of fluid from the fluid container and providing flow data, and a flow control actuator for controlling the flow of fluid through the tube. The apparatus further includes a processor responsive to the pressure data and flow data for determining the downstream resistance of the tube and for providing pressure control data to the pressure device and flow control data to the flow control actuator.

In a fifth facet, the invention is related to a method for pumping infusion fluid from a first fluid container having an outlet communicating with a conduit. The method includes the step of positioning a second fluid container proximal the first fluid container, applying mean pressure within the second container such that pressure is applied to the first fluid container to expel the fluid from the first container into the conduit; and determining the downstream resistance of fluid flow through the conduit.

In another aspect, the step of determining the downstream resistance comprises the steps of setting a first target flow rate from the first container, applying a first pressure within the second fluid container to obtain the first target flow rate, setting a second target flow rate from the first container different than the first target flow rate, applying a second pressure within the second fluid container to obtain the second target flow rate and processing the changes in pressure and changes in target flow rate together. In a more detailed facet, the step of determining the downstream resistance comprises the steps of applying a first pressure within the second fluid container, sensing a first fluid-flow rate at the outlet, applying a second pressure within the second fluid container wherein the second pressure is different than the first pressure, sensing a second fluid-flow rate at the outlet, and processing the changes in pressure and changes in flow together.

In a sixth aspect, the invention is related to a method for pumping infusion fluid from an infusion pump having a first fluid container with an outlet communicating with a conduit, and a second container positioned proximal the first container. The method includes the steps of applying pressure within the second container such that pressure is applied to the first fluid container whereby fluid is expelled from the first container into the conduit and determining the downstream resistance of fluid flow through the conduit.

In a seventh facet, the invention is related to an apparatus for infusing medical fluid into a patient from a first collapsible fluid container. The apparatus includes a standard conduit coupled to the first container to conduct medical fluid from the first container to the patient. An expandable pressure-control container is positioned so as to apply mechanical force against the first container to controllably cause it to collapse and expel its contents to the conduit. A pump is coupled to the pressure-control container to provide fluid under pressure to the pressure-control container to control the amount of expansion of the pressure-control container. This, in turn, controls the mechanical force applied to the first container. The apparatus also includes a pressure sensor coupled to the pressure-control container to sense the pressure of the fluid in the container and to provide pressure signals representative thereof. A flow sensor is coupled to the conduit downstream of the first container to sense the flow of medical fluid through the conduit from the first container and to provide flow signals. A flow control actuator is located downstream of the flow sensor to control the amount of fluid flowing through the conduit. The actuator is responsive to actuator control signals. The apparatus further includes a processor that is coupled to the pump, to the pressure sensor, to the flow sensor, and to the flow control actuator. The processor monitors the flow signals, the pressure signals, and controls the pump and the flow control actuator to achieve a desired flow of fluid through the conduit.

An advantage of the invention is that a relatively inexpensive administration set may be manufactured for use in the disclosed infusion system. A standard straight line infusion set may be used with a computer controlled pressure source and flow restriction as opposed to a peristaltic or other mechanical pumping means to regulate fluid flow under positive pressure, resulting in a less expensive system. The system disclosed and illustrated herein provides the performance and features of a pump without the associated cost of specially designed pumping segments. The system takes advantage of the characteristics of an IV controller system but overcomes the head height pressure limitations by delivering from a pressurized source.

Such an administration set may have a conduit communicating with a collapsible bag, i.e., first container. The conduit may take the form of any well known spike. The administration set may further include a drip chamber, standard PVC tubing, a connector and a patient cannula communicating with the connector. In another approach, the administration set may comprise a collapsible bag with an integral drip chamber and tubing coupled to a patient cannula. The bladder as well may be disposable and come equipped with a simple fluid connection to the pump and pressure sensor combination.

Accordingly, a new and useful infusion system has been provided. The system described and illustrated is closed-loop for more accurate control over the infusion process. Additionally, standard, low cost tubing and administration equipment is used for the disposable part of the system. More expensive parts, such as the processor, display, keyboard, pump and sensors may be reused thus lowering the expense. The ability to determine downstream resistance is provided thus giving the care giver more complete information about the infusion process. Problems that may arise during the infusion process can be detected more readily.

These and other aspects and advantages of the invention will become apparent from the following detailed description and the accompanying drawings, which illustrate by way of example the features of the invention.

BRIEF DESCRIPTION OF THE DRAWINGS

FIG. 3b is a graph depicting small positive and negative flow rate deviations from a mean flow rate which occur during the positive and negative pressure deviations of FIG. 3a.

FIG. 4b is a graph depicting small positive and negative flow rate deviations from a mean flow rate which occur during the positive and negative pressure deviations of FIG. 4a;

DETAILED DESCRIPTION OF PREFERRED EMBODIMENTS

Figure 1:
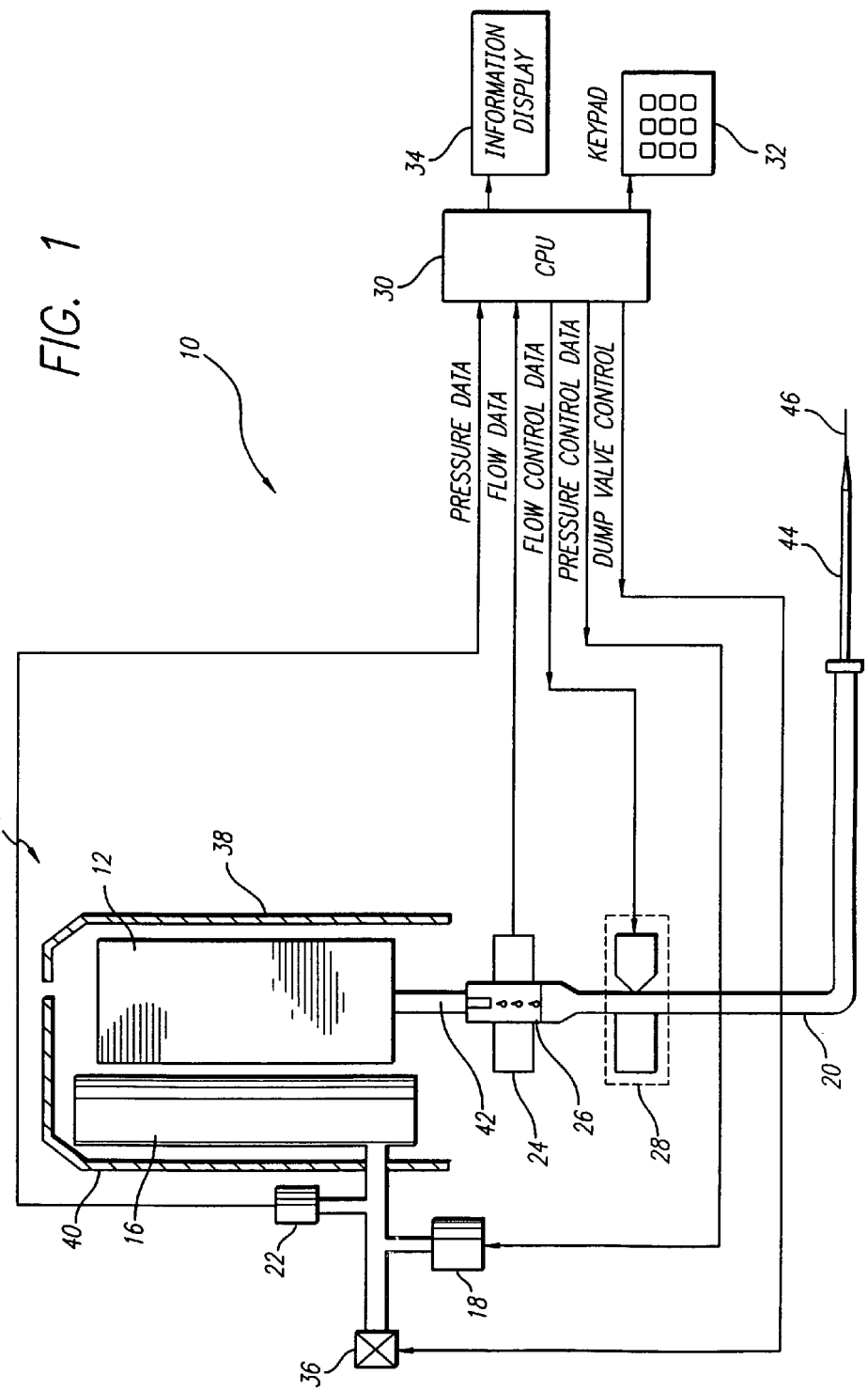
FIG. 1 is a schematic block diagram of an IV infusion system incorporating aspects of the present invention.

Turning now to the drawings, in which like reference numerals are used to designate like or corresponding elements among the several figures, in FIG. 1 there is shown an IV infusion system 10 that utilizes a collapsible fluid container 12 and a pressure bladder 16. The fluid container 12 and the pressure bladder 16 are placed in a housing 14 having a rear panel 40 and a front door 38 with a transparent window (not shown) to allow the user to view the fluid container 12. The bladder 16 can be inflated by use of a pump 18, such as an air or other fluid pump. The bladder 16 is positioned relative to the fluid container 12 such that when the bladder is pressurized, the pressure from the bladder is transferred to the fluid container 12. Thus, the fluid container 12 is placed under pressure by the bladder 16 and the fluid within the container is forced into an IV tubing 20 communicating at one end with the outlet 42 of the container and at the other end with a catheter 44. The catheter 44, in turn, communicates through a cannula 46 with a patient (not shown).

A standard, off-the-shelf, pressure sensor 22 is connected at the inlet end of the bladder 16 to monitor bladder pressure. A drip chamber 26 is located in the IV tubing 20 near the outlet 42 of the fluid container 12. A drop-detecting flow sensor 24 is positioned about the drip chamber 26 to detect fluid drops falling in the drip chamber. The flow sensor 24 may be any well known optical type or capacitive type sensor. Drip chambers and drop-detecting flow sensors are well known to those skilled in the art and no further details with regard to these devices are provided here. A flow control actuator 28 is placed about the IV tubing 20 below the drip chamber 26 to control flow. The actuator 28, in this embodiment, comprises a standard pinching device that subjects the infusion tubing 20 to a degree of pinching, thereby altering the inner diameter or inner opening of the tubing and thereby controlling the amount of flow through the tubing. The flow control actuator 28 may also be a pulse-width-modulation type rather than a degree-of-pinch type.

A processor 30 is provided to accept user input from a keypad 32 and to display pertinent information including downstream resistance, infusion rate, time and volume on an information display 34. The processor 30 also receives pressure and flow-rate data from the pressure sensor 22 and the flow sensor 24 to determine the pressure, the flow rate and the downstream resistance. Based on the signals received from the sensors 22, 24, the processor 30 commands the flow control actuator 28 and the bladder pump 18 in such a way as to regulate the fluid-flow rate to the desired value entered by a user. The pressure bladder 16 establishes the pressure within the IV tubing 20, the drip chamber 26, the catheter 44 and the cannula 46. The flow control actuator 28 applies the appropriate degree of pinch to the IV tubing 20 to regulate the fluid flow rate through the downstream portion of the system, i.e., the portion of the system downstream from the flow control actuator 28, including a portion of the IV tubing 20, the catheter 44 and the cannula 46. In one embodiment, the actuator 28 is a pinching-type valve that is either entirely open with no significant contact with the tubing 20, or entirely closed wherein the tubing 20 is clamped shut. The amount of time that the pinching valve is in the entirely open position and the amount of time that the pinching valve is in the entirely closed position in a predetermined time frame is the duty cycle. Typically, the duty cycle is the comparison of the time the tubing is open to the predetermined time frame. For example, if the tubing is left open for 100 milliseconds out of each 200 milliseconds of time, the duty cycle is 50%.

In operation, the user enters the desired infusion rate into the controller 30 using the keypad 32. The processor 30 determines the pressure $P_0$, i.e., the "mean pressure", and the flow control actuator duty cycle $D_0$, necessary to establish the desired flow rate. The processor 30 controls the pump 18 to inflate the bladder 16 to the mean pressure. The bladder 16 pressure is monitored by the processor 30 through the pressure sensor 22 while the flow rate is monitored through the flow sensor 24. If the sensed flow rate is greater than the desired flow rate, the processor 30 provides flow control data to the flow control actuator 28 to set the duty cycle of the actuator to maintain the flow rate in the downstream portion of the IV tubing 20 at the desired rate. For example, if an infusion rate of 100 ml/hr is desired, but the mean pressure is set at that pressure which establishes a flow rate of 110 ml/hr, the duty cycle would be set at 91% to establish a 100 ml/hr downstream flow rate. If, however, the sensed flow rate is less than the desired flow rate, the processor 30 may either increase the mean pressure at the bladder 16 or decrease the duty cycle of the flow control actuator 28. Naturally, if the duty cycle is set at 100%, i.e., the IV tubing 20 is completely open at all times, the only way to adjust the flow rate is to increase the mean pressure.

Figure 2:
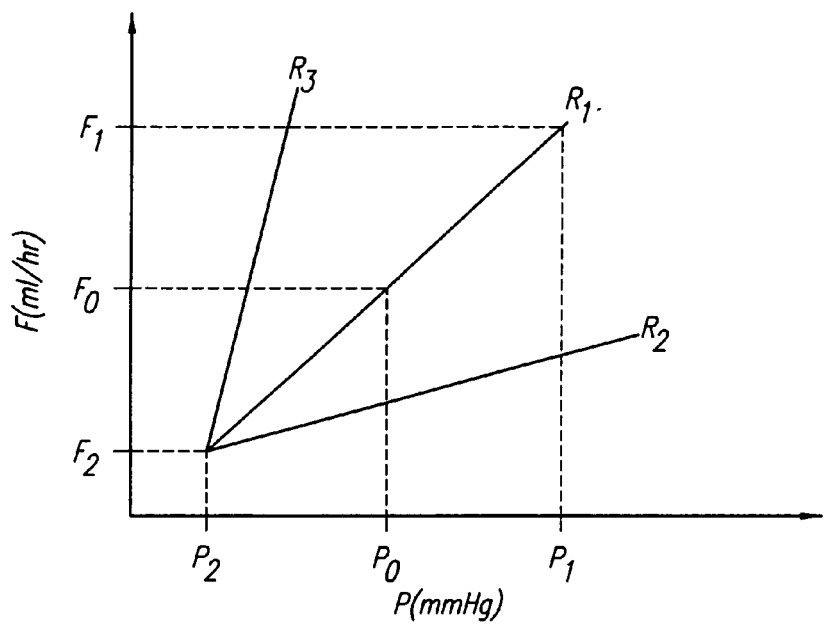
FIG. 2 is a graph depicting pressure verses flow rate relationships for various levels of resistance.

The system 10 is capable of calculating the downstream resistance of the IV tubing 20 either on a periodic basis or as desired intermittently by the operator. To determine the downstream resistance, the processor 30 changes the pressure within the bladder 16 by small positive deviations, $\Delta P$, and negative deviations $-\Delta P$, about the mean pressure and measures the flow rate changes resulting from the pressure changes. As shown in FIG. 2, the flow rate is a function of both pressure and downstream resistance. At a nominal downstream resistance $R_1$, the relationship between pressure and flow rate is rather predictable, that is, an increase or decrease in pressure produces an expected corresponding increase or decrease in flow rate. At a high resistance $R_2$, a significant increase or decrease in pressure produces only a slight increase or decrease in flow rate. In the extreme situation where the IV tubing 20 is completely occluded, the resistance line would be substantially horizontal and no amount of pressure change will cause fluid flow change. In this situation, the flow rate will probably be zero. At a low resistance $R_3$, a slight increase or decrease in pressure produces a significant increase or decrease in flow rate. In the extreme situation where the IV tubing 20 is completely unobstructed, e.g., the IV needle is no longer in the patient, the resistance line may have a large slope depending on the sizes of the tubing, catheter 44 and the cannula 46 and the change in flow rates will be large in response to pressure changes.

Figure 3A:
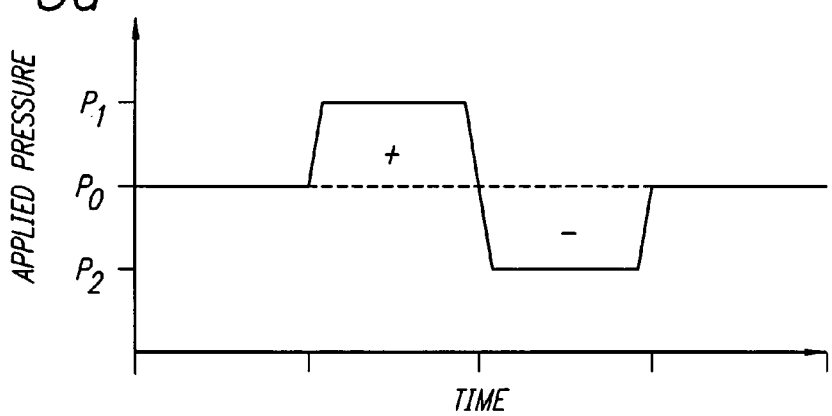
FIG. 3a is a graph depicting small positive and negative pressure deviations from a mean pressure which occur during resistance calculations performed in accordance with the one embodiment of the present invention.
Figure 3B:
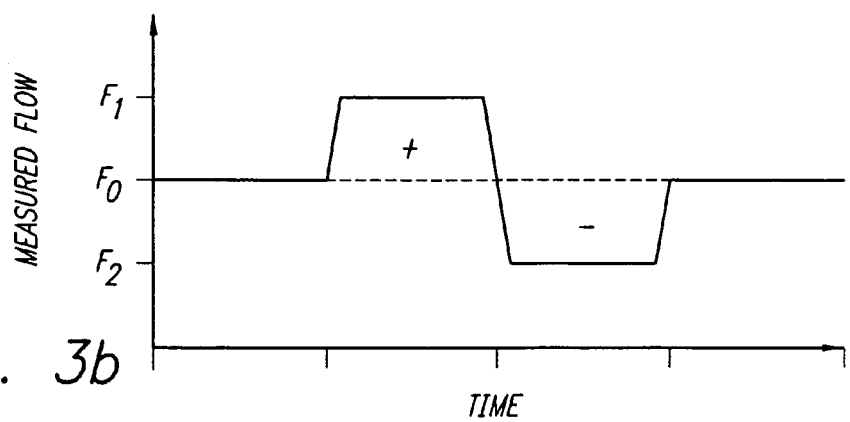

To measure the downstream resistance, i.e., the resistance downstream of the flow control actuator 28, the flow rate $F_0$ through the drip chamber 26 at pressure $P_0$ is first measured using data from the flow sensor 24. The pressure within the bladder 16 is then increased above the mean pressure $P_0$ by $\Delta P$ to pressure $P_1$, as shown in FIG. 3*a*. The flow rate $F_1$, as shown in FIG. 3*b*, is then measured using data from the flow sensor 24. The downstream resistance is than calculated using the following equation:

$$R = \frac{P_1 - P_0}{F_1 - F_0} \quad \text{(Eq. 1)}$$

A subsequent resistance measurement is obtained by decreasing the pressure within the bladder 16 below the mean pressure $P_0$ by $-\Delta P$ to pressure $P_2$. The flow rate $F_2$ is then measured using data from the flow sensor 24. The downstream resistance is than calculated using the following equation:

$$R = \frac{P_1 - P_2}{F_1 - F_2} \quad \text{(Eq. 2)}$$

Once the resistance measurement is complete, the bladder pressure is reset to the initial mean pressure $P_0$.

Figure 4A:
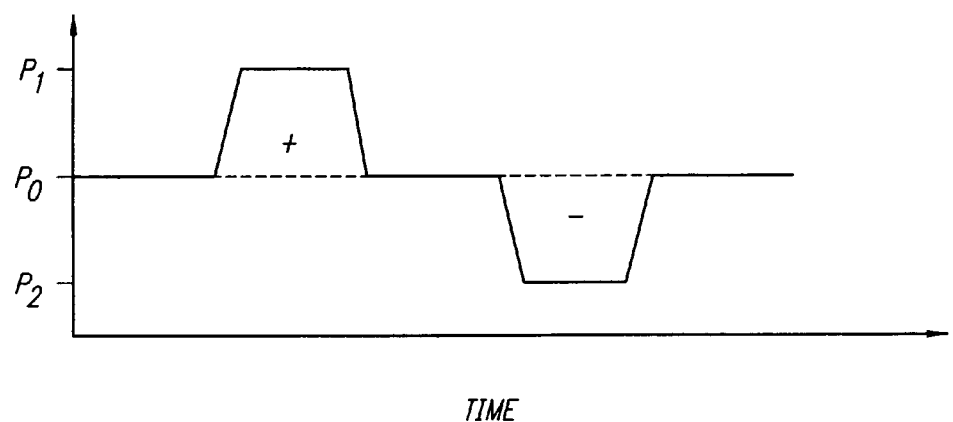
FIG. 4a is a graph depicting small positive and negative pressure deviations from a mean pressure which occur during resistance calculations performed in accordance with another embodiment of the present invention.
Figure 4B:
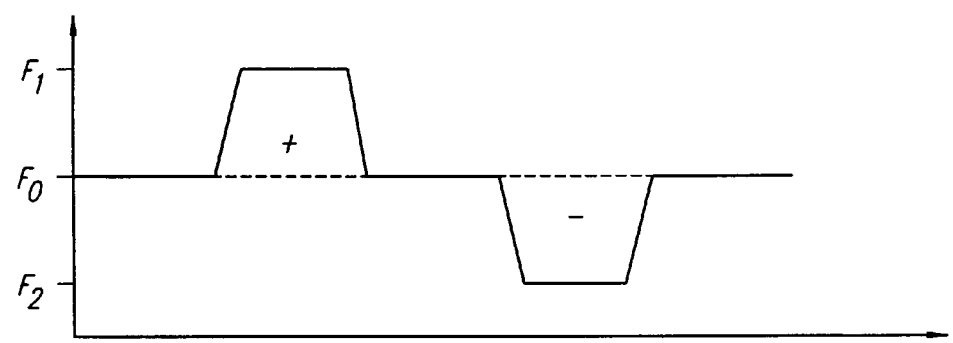

In an alternate embodiment, as shown in FIGS. 4*a* and 4*b*, the subsequent resistance measurement is determined by resetting the pressure to the initial pressure $P_0$ measuring the flow rate $F_0$ and then decreasing the pressure within the bladder 16 below the mean pressure $P_0$ by $-\Delta P$ to pressure $P_2$. The downstream resistance is than calculated using the following equation:

$$R = \frac{P_0 - P_2}{F_0 - F_2} \quad \text{(Eq. 3)}$$

It is noted that in general there is a pressure differential between the pressure at the top of the fluid in the fluid container 12, i.e., the bladder 16 pressure, and the pressure at the catheter 44. This pressure differential is a result of the fluid column in the IV tubing 20 between the fluid container 12 and the catheter 44. The fluid column causes the pressure at the catheter to be greater than the pressure at the fluid container 12. The difference between the two pressures is a function of the vertical distance between the fluid container 12 and the catheter 44, the greater the distance, the greater the pressure difference. As long as the vertical distance between the fluid container 12 and the catheter 44 remains relatively constant, this pressure differential remains constant. Because the resistance measurement itself is differential, this pressure differential cancels out and, in general, does not affect the accuracy of the resistance measurement.

The frequency of downstream resistance measurement may be set by the processor or set by the operator through the keypad 32. For the pressure pattern depicted in FIG. 3a, two consecutive frequency measurements are calculated using Eqs. 1 and 2. These two measurements may be averaged to obtain a single resistance measurement. The time between the next pair of positive and negative pressure deviations defines the frequency. For the pressure pattern depicted in FIG. 4a, the positive pressure deviation provides a resistance measurement using Eq. 1. The negative pressure deviation provides a resistance measurement using Eq. 3. The time between the positive and negative deviations may define the frequency. In the alternative, if the positive and negative deviations occur substantially close to each other they may be considered a deviation pair, similar to the deviation pair of FIG. 3a, and the time between the next pair of positive and negative pressure deviations defines the frequency. A resistance measurement may also be received on command by the operator through the keypad 32.

It is clear from equations 1 through 3 that a large change in pressure with a small change in flow results in a large number for the resistance, perhaps indicating an obstructed downstream line or an infiltration. Vice versa, a small change in pressure with a large change in flow results in a small number for resistance, perhaps indicating that the cannula has completely withdrawn from the patient for some reason.

During resistance measuring, the flow control actuator 28 operates at a fixed duty cycle, thereby maintaining the desired flow rate in the downstream portion of the system. The flow control actuator 28 compresses the IV tubing 20 in accordance with the fixed duty cycle selected to maintain the desired flow rate in the downstream portion of the system. The average flow rate within the drip chamber 26 is maintained by the small positive $\Delta P$ and small negative $-\Delta P$ pressure deviations from the mean $P_0$, as shown in FIGS. 3a and 4a, which in the aggregate, cancel each other out to maintain an average flow rate within the drip chamber substantially equal to the desired flow rate.

It is significant that the pressure deviations from $P_0$ be both positive and negative, otherwise, were the pressure deviations only positive, the average flow rate would be higher than the desired flow rate. Conversely, were the pressure deviations only negative, the average flow rate would be lower than the desired flow rate.

Figure 5:
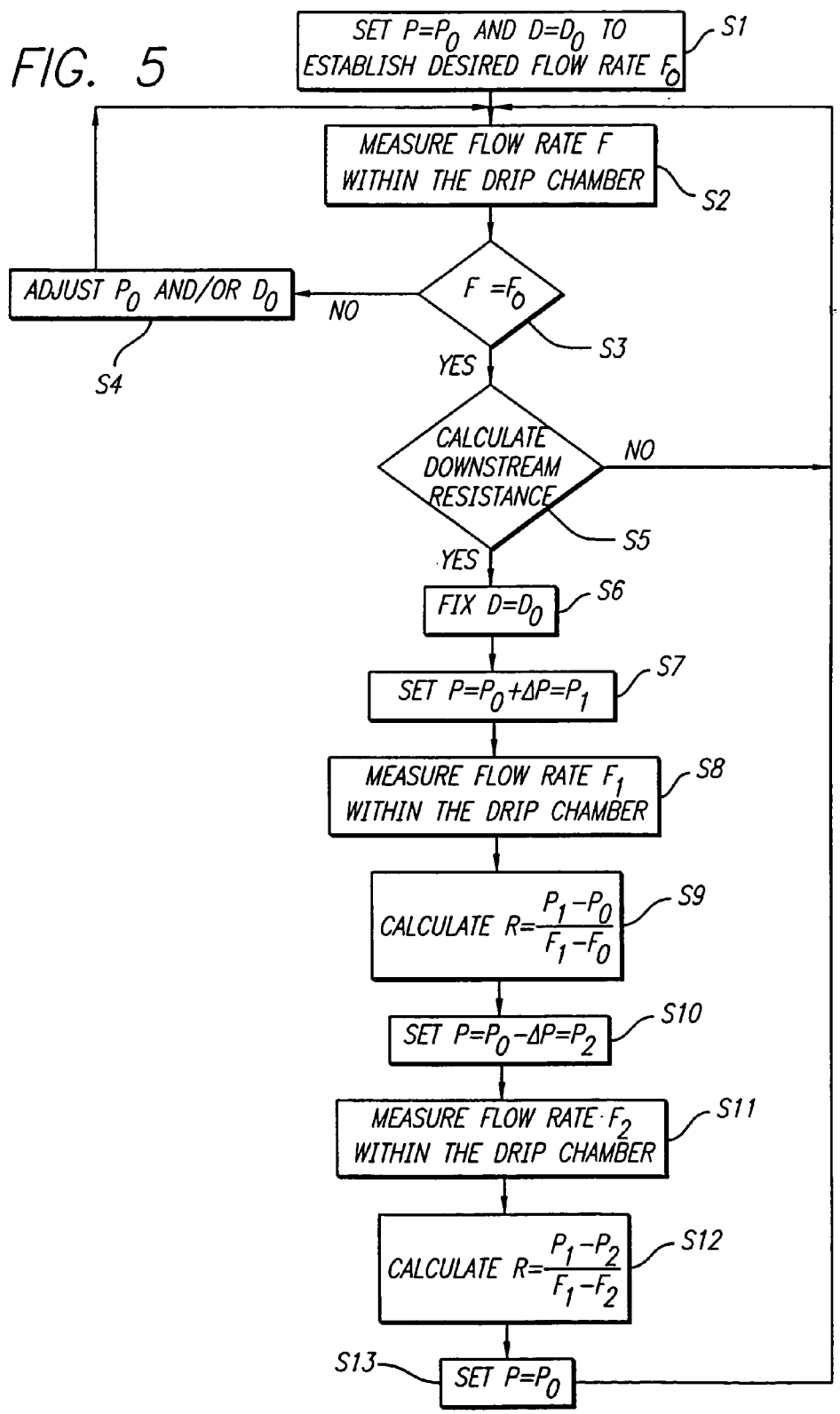
FIG. 5 is a flow chart of the downstream resistance measurement process in accordance with one embodiment of the present invention.

A flow chart of one version of operation of the infusion system, including a downstream resistance measurement under the pressure deviation scenario of FIG. 3a, is provided in FIG. 5. In step S1, the pressure P of the bladder 16 is set to $P_0$ and the duty cycle D of the flow control actuator 28 is set to $D_0$ to establish a flow rate $F_0$. In step S2, the flow rate F within the drip chamber 26 is measured. In step S3, it is determined whether the measured flow rate F equals the desired flow rate $F_0$. If no, then the pressure $P_0$ and/or duty cycle $D_0$ are adjusted in step S4 and the process returns to step S2.

If the measured flow rate F equals the desired flow rate $F_0$, then in step S5 it is determined whether it is time to perform a resistance measurement. If it is not yet time, the process returns to step S2. If it is time to perform a resistance measurement, the duty cycle is fixed at $D_0$ in step S6. In step S7, the bladder pressure P is set to $P_0+\Delta P=P_1$. In step S8, the flow rate $F_1$ within the drip chamber 26 is measured. In step S9, the downstream resistance is calculated using Eq. 1. In step S10, the bladder pressure P is set to $P_0-\Delta P=P_2$. In step S11, the flow rate $F_2$ within the drip chamber 26 is measured. In step S12, the downstream resistance is calculated using Eq. 2. In step S13, the bladder pressure P is set to $P_0$ and the process returns to step S2.

Figure 6:
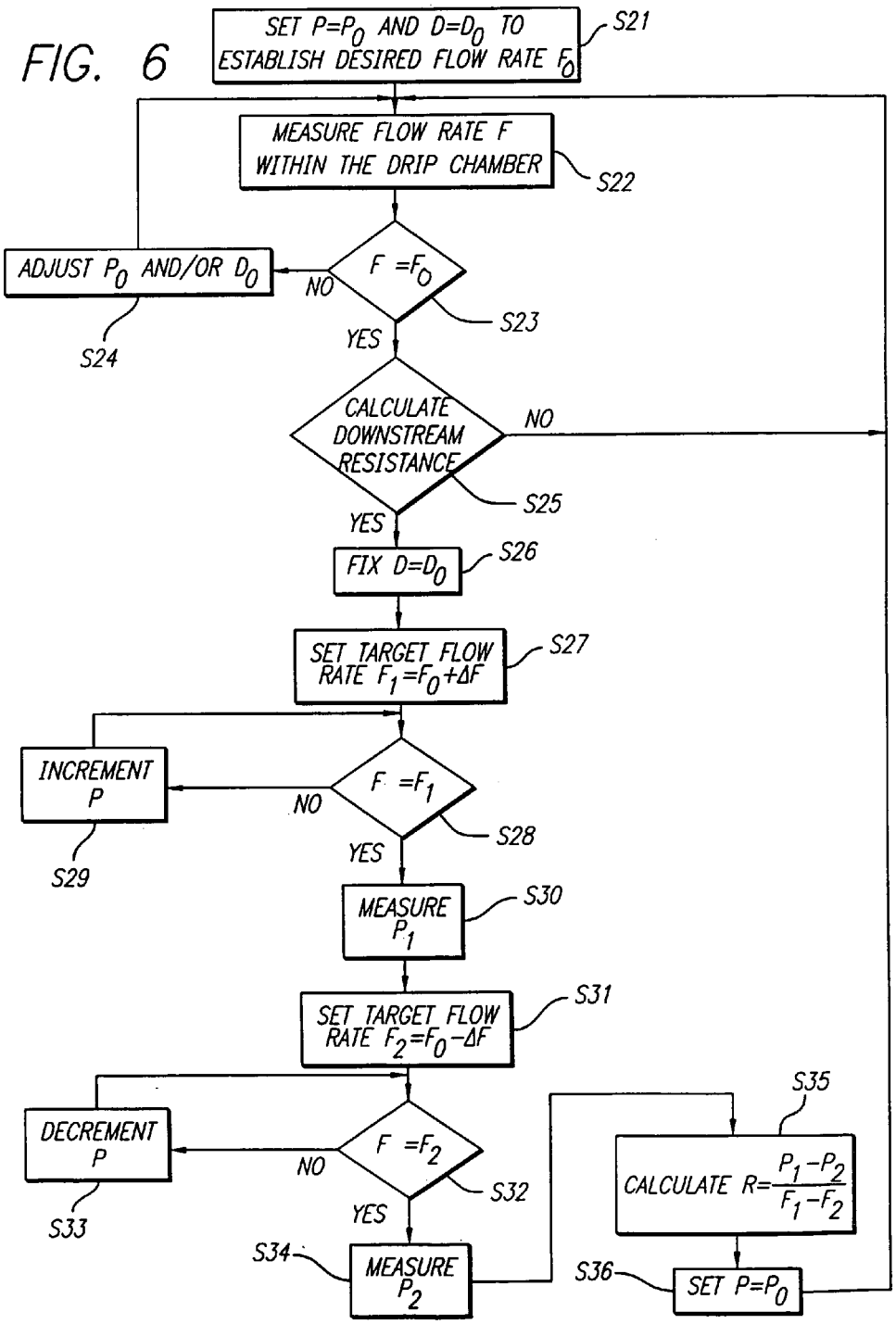
FIG. 6 is a flow chart of the downstream resistance measurement process in accordance with another embodiment of the present invention.

A flow chart of another version of operation of the infusion system, also including a downstream resistance measurement under the pressure deviation scenario of FIG. 3a, is provided in FIG. 6. In step S21, the pressure P of the bladder 16 is set to $P_0$ and the duty cycle D of the flow control actuator 28 is set to $D_0$ to establish a flow rate $F_0$. In step S22, the flow rate F within the drip chamber 26 is measured. In step S23, it is determined whether the measured flow rate F equals the desired flow rate $F_0$. If no, then the pressure $P_0$ and/or duty cycle $D_0$ are adjusted in step S24 and the process returns to step S22.

If the measured flow rate F equals the desired flow rate $F_0$, then in step S25 it is determined whether it is time to perform a resistance measurement. If it is not yet time, the process returns to step S22. If it is time to perform a resistance measurement, the duty cycle is fixed at $D_0$ in step S26. In step S27, a first target flow rate $F_1$ is set to $F_0+\Delta F$. In step S28, it is determined whether the measured flow rate F equals the first target flow rate $F_1$. If no, then the pressure $P_0$ is increased by an incremental amount in step S29 and the process returns to step S28. If yes, then in step S30 the pressure $P_1$ is measured, where $P_1$ is the pressure required to achieve the first target flow rate $F_1$.

In step S31, a second target flow rate $F_2$ is set to $F_0-\Delta F$. In step S32, it is determined whether the measured flow rate F equals the second target flow rate $F_2$. If no, then the pressure $P_0$ is decreased by an incremental amount in step S33 and the process returns to step S32. If yes, then in step S34 the pressure $P_2$ is measured, where $P_2$ is the pressure required to achieve the second target flow rate $F_2$. In step S35, the downstream resistance is calculated using Eq. 2. In step S36, the bladder pressure P is set to $P_0$ and the process returns to step S22.

In measuring the resistance by determining changes in pressure in response to changes in flow rate as opposed to determining changes in flow rate in response to changes in pressure, this version of operation is better able to maintain the average flow rate within the drip chamber near $F_0$.

During operation, the processor monitors for alarm conditions. Such alarm conditions may include system occlusion conditions and system disconnect conditions. A system occlusion is detected when the flow data provided by the flow sensor 24 indicates a flow rate that is less than expected for a given applied pressure. The larger the flow-rate deviates from the expected flow rate the more significant the system occlusion. In the extreme case, if the flow rate is zero, a complete occlusion is likely. A system occlusion may occur in the downstream portion of the system or in the portion of the system between the fluid container 12 and the flow control actuator 28.

A system disconnect is detected when the flow data provided by the flow sensor 24 indicates a flow rate that is significantly greater than expected for a given applied pressure. A system disconnect may occur when the tubing 20 disconnects from the catheter 44, when the catheter disconnects from the cannula 46 or when the cannula disconnects from the patient.

In the event of an alarm condition, the processor 30 may, if desired, automatically activate a dump valve 36 to rapidly depressurize the bladder 16 thereby stopping further fluid flow from the fluid container 12 to the IV tubing 20. The processor 30 may also stop signaling the flow control actuator 28 causing it to pinch the IV tubing 20 completely shut thereby stopping further fluid flow to the patient.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An apparatus for pumping infusion fluid from a first fluid container having an output communicating with a conduit, said apparatus comprising:
    a second fluid container positioned adjacent to the first fluid container and configured for application of pressure to the first fluid container to expel the fluid from the first fluid container;
    a flow control actuator coupled to the conduit for controlling the desired flow rate;
    a pressure sensor coupled to the second fluid container adapted to sense pressure in the second fluid container and provide a pressure signal in response to the pressure sensed;
    a flow sensor coupled to the conduit and adapted to sense fluid flow in the conduit and provide a flow signal in response to the fluid flow sensed; and
    a processor operatively coupled to said second fluid container for controlling said application of pressure and operatively coupled to said flow control actuator for controlling said desired flow rate, wherein said processor is configured to determine the downstream resistance in the conduit by selectively applying a plurality of pressure values to said second fluid container to obtain a plurality of pressure signals from said pressure sensor and a plurality of flow signals from said flow sensor, and wherein said processor computes said downstream resistance using a quotient of the difference between two of said plurality of pressure signals and a corresponding two of said plurality of flow signals.

2. The apparatus of claim 1, further comprising:
    a pump coupled to the second fluid container for providing said application of pressure to the second fluid container.

3. The apparatus of claim 2 wherein the pump is responsive to pressure control data from the processor.

4. The apparatus of claim 1, wherein said flow control actuator is coupled to the conduit downstream from the flow sensor.

5. The apparatus of claim 4 wherein the flow control actuator is responsive to flow control data from the processor.

6. The apparatus of claim 1 wherein the second fluid container includes an input, and further comprising a dump valve coupled to the input of the second fluid container.

7. The apparatus of claim 6 wherein the dump valve is responsive to dump valve control data from the processor.

8. The apparatus of claim 1 further comprising a display responsive to the processor for displaying downstream resistance measurements.

9. The apparatus of claim 1 further comprising a user input device, coupled to the processor, for entering desired flow-rate data.

10. The apparatus of claim 1 wherein the processor determines the downstream resistance by controlling the pressure applied to the fluid in the first container to cause a plurality of different flow rates to exist at the output of the first container, receiving the flow data resulting from each flow rate and determining the fluid resistance by processing changes in applied pressure and changes in flow together.

11. The apparatus of claim 1 wherein the processor determines the downstream resistance by setting a plurality of target flow rates, measuring the pressure applied to the fluid in the first container to cause each of the plurality of target flow rates to exist at the output of the first fluid container, receiving the flow data resulting from each target flow rate and determining the fluid resistance by processing changes in applied pressure and changes in flow together.

12. The apparatus of claim 11 wherein the plurality of target flow rates deviate from a mean flow rate by small positive and negative amounts to maintain an average flow rate substantially equal to the mean flow rate.

13. A method for pumping infusion fluid from a collapsible fluid container having an outlet communicating with a conduit, said method comprising:
    inflating a pressure bladder located in relation to the collapsible fluid container such that the pressure bladder applies pressure to the collapsible fluid container when the pressure bladder is inflated;
    applying a mean pressure within the pressure bladder such that the fluid from the collapsible fluid container is expelled from the outlet at a mean flow rate;
    sensing a pressure within the pressure bladder;
    sensing a flow rate of fluid in the conduit; and
    determining a measure of resistance to fluid flow through the conduit based on the sensed pressure and the sensed flow rate, wherein said determining the measure of resistance comprises:
    applying a first pressure within the pressure bladder;
    sensing a first fluid-flow rate at the outlet corresponding to the first pressure;
    applying a second pressure within the pressure bladder wherein the second pressure is different than the first pressure;
    sensing a second fluid-flow rate at the outlet corresponding to the second pressure; and
    processing a difference between the first and second pressures together with a difference between the first and second fluid-flow rates.

14. The method of claim 13 wherein one of either the first or second pressure is the mean pressure.

15. The method of claim 13 wherein the first pressure and the second pressure deviate from the mean pressure by a positive amount and a negative amount respectively to maintain an average pressure substantially equal to the mean pressure.

16. A method for pumping infusion fluid from a collapsible fluid container having an outlet communicating with a conduit, said method comprising:
inflating a pressure bladder located in relation to the collapsible fluid container such that the pressure bladder applies pressure to the collapsible fluid container when the pressure bladder is inflated;
applying a mean pressure within the pressure bladder such that the fluid from the collapsible fluid container is expelled from the outlet at a mean flow rate;
sensing a pressure within the pressure bladder;
sensing a flow rate of fluid in the conduit; and
determining a measure of resistance to fluid flow through the conduit based on the sensed pressure and the sensed flow rate, wherein said determining the measure of resistance comprises:
setting a first target flow rate from the collapsible fluid container;
applying a first pressure within the pressure bladder to obtain the first target flow rate;
setting a second target flow rate from the collapsible fluid container different than the first target flow rate;
applying a second pressure within the pressure bladder to obtain the second target flow rate;
processing a difference between the first and second pressures together with a difference between the first and second target flow rates.

17. The method of claim 16 wherein one of either the first or second target flow rates is the mean flow rate.

18. The method of claim 16 wherein the first target flow rate and the second target flow rate deviate from the mean flow rate by a positive amount and a negative amount respectively to maintain an average flow rate substantially equal to the mean flow rate.

19. The method of claim 16 further comprising the steps of maintaining the flow rate substantially constant while determining the measure of resistance.

20. A method for pumping infusion fluid from an infusion pump having a collapsible fluid container in which a medical fluid is stored with an outlet communicating with a conduit and a pressure bladder positioned proximal the collapsible fluid container, said method comprising the steps of:
applying pressure within the pressure bladder to inflate the bladder to an extent such that it contacts and applies pressure to the collapsible fluid container to expel medical fluid from the collapsible fluid container into the conduit to create fluid flow;
measuring pressure within the pressure bladder and providing pressure signals;
measuring actual fluid flow through the conduit, and providing fluid flow signals; and
determining a measure of resistance to fluid flow through the conduit, including processing the pressure signals representative of the pressure within the pressure bladder and processing the flow signals representative of the fluid flow in the conduit, wherein said determining the measure of resistance comprises:
applying a plurality of different pressures to the pressure bladder to cause a plurality of different flow rates to exist at the outlet of the collapsible fluid container;
receiving a pressure signal for each of the plurality of different pressures applied to the pressure bladder;
receiving a flow signal for each of the plurality of different flow rates at the outlet of the collapsible fluid container; and
processing changes in the flow signals and changes in the pressure signals together.

21. The method of claim 20 wherein the step of causing a plurality of different flow rates to exist at the outlet of the collapsible fluid container comprises the step of applying a plurality different pressures within the pressure bladder.

22. The method of claim 20 wherein the step of causing a plurality of different flow rates to exist at the outlet of the collapsible fluid container comprises the steps of:
setting a plurality of different target flow rates; and
for each target flow rate, applying within the pressure bladder, a pressure required to achieve the target flow rate.

23. An apparatus for pumping infusion fluid from a collapsible fluid container having an output communicating with a conduit, said apparatus comprising:
a housing within which is disposed a collapsible fluid container having an output communicating with a conduit;
a pressure bladder positioned within the housing in close proximity to the collapsible fluid container such that when the pressure bladder is inflated it applies pressure to collapse the collapsible fluid container and thereby expel the fluid from the collapsible fluid container into the conduit;
a pressure sensor coupled to the pressure bladder, the pressure sensor adapted to measure pressure in the pressure bladder and provide a pressure signal in response to the pressure within the pressure bladder;
a flow sensor separate from the pressure sensor, the flow sensor coupled to the conduit and adapted to measure fluid flow in the conduit and provide a flow signal in response to the fluid flow;
a flow control actuator coupled to the conduit for setting a desired flow rate; and
a processor operatively coupled to said pressure bladder for controlling the pressure in said pressure bladder and operatively connected to said flow control actuator for controlling the desired flow rate, said processor configured to receive said pressure signal and said flow signal and to determine the resistance to the flow of infusion fluid through the conduit based on a plurality of samples of pressure signals and a corresponding plurality of samples of flow signals.

24. The apparatus of claim 23, wherein said pressure bladder further comprises a pump coupled to the pressure bladder for controlling the pressure within the pressure bladder by inflation of the pressure bladder, the pump operatively connected to the processor and is responsive to pressure control signals from the processor.

25. The apparatus of claim 23, wherein said flow control actuator is coupled to the conduit downstream from the flow sensor, wherein the flow control actuator is responsive to flow control signals from the processor.

26. The apparatus of claim 23 further comprising a dump valve coupled to the pressure bladder, the dump valve operatively connected to the processor and is responsive to dump valve control signals from the processor to reduce pressure in the pressure bladder.

27. The apparatus of claim 23 wherein the processor:
controls the pressure applied by the pressure bladder to the fluid in the collapsible fluid container to cause a plurality of different flow rates to exist at the output of the collapsible fluid container;

receives the flow signals resulting from each of the different flow rates; and processes changes in applied pressure together with changes in flow signals to determine the measure of downstream resistance.

28. The apparatus of claim 23 wherein the processor:

sets a plurality of target flow rates, measures the pressure applied to the fluid in the first container to cause each of the plurality of target flow rates to exist at the output of the collapsible fluid container, receives the flow signals resulting from each target flow rate, and processes changes in applied pressure and changes in flow together to determine the measure of downstream resistance.

29. A method for pumping infusion fluid from an infusion pump having a collapsible fluid container in which a medical fluid is stored with an outlet communicating with a conduit and a pressure bladder positioned proximal the collapsible fluid container, said method comprising:

setting a desired fluid flow rate through the conduit using a flow control actuator connected to said conduit;

applying a desired pressure within the pressure bladder to inflate the bladder to an extent such that it contacts and applies external pressure to the collapsible fluid container to expel medical fluid from the collapsible fluid container into the conduit;

measuring pressure within the pressure bladder to obtain a pressure signal;

measuring actual fluid flow rate through the conduit at the outlet of the collapsible fluid container to obtain a flow signal; and determining a measure of resistance to fluid flow through the conduit when said actual fluid flow rate is equivalent to the desired fluid flow rate, wherein said determining the measure of resistance comprises:

applying a plurality of different pressures to the pressure bladder to cause a plurality of different flow rates to exist at the outlet of the collapsible fluid container;

obtaining one of said pressure signal for each of the plurality of different pressures applied to the pressure bladder;

obtaining one of said flow signal for each of the plurality of different flow rates at the outlet of the collapsible fluid container; and generating said measure of resistance by computing the quotient of the difference in the pressure signals and the difference in the flow signals.

30. The method of claim 29, further comprising:

adjusting the desired pressure applied within the pressure bladder when the actual fluid flow rate is not equivalent to the desired fluid flow rate.

31. The method of claim 29, further comprising:

adjusting the flow control actuator when the actual fluid flow rate is not equivalent to the desired fluid flow rate.

32. The method of claim 29, further comprising:

releasing the pressure applied to the pressure bladder when the pressure contained therein is greater than a threshold pressure level.

33. The method of claim 29, further comprising:

releasing the pressure applied to the pressure bladder when it is desired to stop the infusion.

34. The method of claim 29, further comprising:

displaying the measure of resistance of fluid flow through the conduit.

35. A method for pumping infusion fluid from an infusion pump having a collapsible fluid container in which a medical fluid is stored with an outlet communicating with a conduit and a pressure bladder positioned proximal the collapsible fluid container, said method comprising:

setting a desired fluid flow rate through the conduit using a flow control actuator connected to said conduit;

applying a desired pressure within the pressure bladder to inflate the bladder to an extent such that it contacts and applies external pressure to the collapsible fluid container to expel medical fluid from the collapsible fluid container into the conduit;

measuring pressure within the pressure bladder to obtain a pressure signal;

measuring actual fluid flow rate through the conduit at the outlet of the collapsible fluid container to obtain a flow signal; and determining a measure of resistance to fluid flow through the conduit when said actual fluid flow rate is equivalent to the desired fluid flow rate, wherein said determining the measure of resistance comprises:

applying a first pressure within the pressure bladder;

sensing a first fluid-flow rate at the outlet corresponding to the first pressure;

applying a second pressure within the pressure bladder wherein the second pressure is different than the first pressure;

sensing a second fluid-flow rate at the outlet corresponding to the second pressure; and generating said measure of resistance by computing the quotient of the difference between the first and second pressure signals and the difference between the first and second fluid-flow rate signals.

36. The method of claim 35, further comprising:

adjusting the desired pressure applied within the pressure bladder when the actual fluid flow rate is not equivalent to the desired fluid flow rate.

37. The method of claim 35, further comprising:

adjusting the flow control actuator when the actual fluid flow rate is not equivalent to the desired fluid flow rate.

38. The method of claim 35, further comprising:

releasing the pressure applied to the pressure bladder when the pressure contained therein is greater than a threshold pressure level.

39. The method of claim 35, further comprising:

releasing the pressure applied to the pressure bladder when it is desired to stop the infusion.

40. The method of claim 35, further comprising:

displaying the measure of resistance of fluid flow through the conduit.

* * * * *